United States Patent
Song et al.

(10) Patent No.: US 11,227,389 B2
(45) Date of Patent: *Jan. 18, 2022

(54) INTERACTIVE CLINICAL DIAGNOSIS REPORT SYSTEM

(71) Applicant: Keya Medical Technology Co., Ltd., Beijing (CN)

(72) Inventors: Qi Song, Seattle, WA (US); Hanbo Chen, Seattle, WA (US); Zheng Te, Beijing (CN); Youbing Yin, Kenmore, WA (US); Junjie Bai, Seattle, WA (US); Shanhui Sun, Princeton, NJ (US)

(73) Assignee: KEYA MEDICAL TECHNOLOGY CO., LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/013,632

(22) Filed: Sep. 6, 2020

(65) Prior Publication Data

US 2020/0402237 A1    Dec. 24, 2020

Related U.S. Application Data (63) Continuation of application No. 16/154,681, filed on Oct. 8, 2018, now Pat. No. 10,803,579.

(Continued)

(51) Int. Cl.
*G06K 9/00* (2006.01)
*G06T 7/00* (2017.01)
(Continued)

(52) U.S. Cl.
CPC .............. *G06T 7/0012* (2013.01); *G06N 3/02* (2013.01); *G16H 15/00* (2018.01); *G16H 30/20* (2018.01); *G16H 30/40* (2018.01); *G16H 50/20* (2018.01)

(58) Field of Classification Search
CPC ........ G06T 7/0012; G06N 3/02; G16H 15/00; G16H 30/20; G16H 30/40; G16H 50/20; G06K 9/00; G06K 9/00124
See application file for complete search history.

(56) References Cited

U.S. PATENT DOCUMENTS 7,261,691 B1    8/2007  Asomani
7,302,164 B2   11/2007  Wright et al.
(Continued)

FOREIGN PATENT DOCUMENTS

CN    106569673 A    4/2017
CN    106780460 A    5/2017
(Continued)

OTHER PUBLICATIONS

Simonyan, K. et al., "Very Deep Convolutional Networks for Large-Scale Image Recognition", arXiv:1409.1556v6 [cs.CV] Apr. 10, 2015; 14 pages.
(Continued)

*Primary Examiner* — Amir Alavi
(74) *Attorney, Agent, or Firm* — Bayes PLLC (57) ABSTRACT

Embodiments of the disclosure provide systems and methods for generating a diagnosis report based on a medical image of a patient. The system includes a communication interface configured to receive the medical image acquired by an image acquisition device. The system further includes at least one processor. The at least one processor is configured to detect a medical condition based on the medical image and automatically generate text information describing the medical condition. The at least one processor is further configured to construct the diagnosis report, where the diagnosis report includes at least one image view showing the medical condition and a report view including the text information describing the medical condition. The system
(Continued)

tem also includes a display configured to display the diagnosis report.

20 Claims, 4 Drawing Sheets

Related U.S. Application Data (60) Provisional application No. 62/572,114, filed on Oct. 13, 2017.

(51) Int. Cl.
  *G16H 50/20* (2018.01)
  *G06N 3/02* (2006.01)
  *G16H 30/40* (2018.01)
  *G16H 30/20* (2018.01)
  *G16H 15/00* (2018.01)

(56) References Cited

U.S. PATENT DOCUMENTS

| | | | |
|---|---|---|---|
| 7,346,203 B2 | 3/2008 | Turek et al. | |
| 7,711,583 B2 | 5/2010 | Epstein et al. | |
| 7,894,676 B2 | 2/2011 | Iizuka et al. | |
| 8,401,260 B2 | 3/2013 | Nirmal et al. | |
| 8,478,611 B2 * | 7/2013 | Epstein | G16H 20/10 705/3 |
| 9,594,878 B2 * | 3/2017 | Silva | G06Q 10/101 |
| 9,824,457 B2 | 11/2017 | Wenzel et al. | |
| 9,846,938 B2 | 12/2017 | Steigauf et al. | |
| 9,959,386 B2 | 5/2018 | Ohad et al. | |
| 10,026,508 B2 * | 7/2018 | Silva | G16H 50/80 |
| 10,198,816 B2 * | 2/2019 | Steigauf | G16H 40/20 |
| 10,248,759 B2 | 4/2019 | Larcom et al. | |
| 10,395,420 B2 | 8/2019 | Vilsmeier | |
| 10,579,234 B2 | 3/2020 | Reichter | |
| 10,614,196 B2 * | 4/2020 | Maitra | G16H 50/70 |
| 10,734,101 B2 * | 8/2020 | Rajan | G16H 10/60 |
| 10,803,579 B2 * | 10/2020 | Song | G16H 30/20 |
| 10,811,125 B2 * | 10/2020 | Bao | G06F 16/35 |
| 10,892,056 B2 * | 1/2021 | Xie | G06F 40/20 |
| 10,937,164 B2 * | 3/2021 | Steigauf | G06K 9/4623 |
| 10,937,552 B2 * | 3/2021 | Ghogawala | G16H 30/40 |
| 11,069,432 B2 * | 7/2021 | Guo | G16H 50/70 |
| 2006/0284732 A1 | 12/2006 | Brock-Fisher | |
| 2012/0059664 A1 | 3/2012 | Georgiev et al. | |
| 2015/0112722 A1 | 4/2015 | Dees et al. | |
| 2017/0098153 A1 | 4/2017 | Mao et al. | |
| 2017/0132526 A1 | 5/2017 | Cohen et al. | |
| 2019/0114766 A1 | 4/2019 | Song et al. | |
| 2019/0139218 A1 | 5/2019 | Song et al. | |
| 2019/0313903 A1 | 10/2019 | McKinnon | |
| 2020/0020449 A1 | 1/2020 | Brazil | |

FOREIGN PATENT DOCUMENTS

| | | |
|---|---|---|
| CN | 107145910 A | 9/2017 |
| CN | 108665055 A | 10/2018 |

OTHER PUBLICATIONS

Huang, Gao et al., "Densely Connected Convolutional Networks", Proceedings of IEEE Conference on Computer Vision and Pattern Recognition. 2017; 9 pages.

Hochreiter, Sepp et al. "Long Short-Term Memory", Neural Computation, 9(8): pp. 1735-1780, 1997.

Cho, Kyunghyun et al., "On the Properties of Neural Machine Translation: Encoder-Decoder Approaches", arXiv:1409.1259v2 [cs.CL] Oct. 7, 2014, 9 pages.

First Office action issued in related Chinese Application No. 201811190189.X, dated Apr. 17, 2020, 10 pages.

First Office Action issued in related Chinese Application No. 201811308886.0, dated Aug. 10, 2020, 9 pages.

* cited by examiner

INTERACTIVE CLINICAL DIAGNOSIS REPORT SYSTEM

CROSS REFERENCE TO RELATED APPLICATION

The present application is a continuation of U.S. application Ser. No. 16/154,681 filed Oct. 8, 2018, which claims the benefits of priority to U.S. Provisional Application No. 62/572,114, filed Oct. 13, 2017. Each application is incorporated herein by reference in its entirety.

TECHNICAL FIELD

The present disclosure relates to a diagnosis report system, and more particularly to, an interactive diagnosis report system that automatically generates a diagnosis report based on medical images of a patient, allows a user to edit or otherwise interact with the medical images, and updates the diagnostic report according to the user interaction.

BACKGROUND

Radiologists read medical images to detect abnormalities and make diagnosis of diseases. Writing diagnosis report is also part of routine jobs for radiologists/clinicians. The diagnosis report often conforms with report templates and clinical standards. Diagnosis reports are usually prepared by a radiologist to record his diagnosis. The radiologist may also perform certain measurements, e.g., the size of a tumor, and record the measurements in the report. If the radiologist wants to include an image in his report to be illustrative, he typically has to transfer the image between different platforms, and then manually copy and paste it into the report. Generating a diagnosis report is thus tedious and inefficient. Some improved report systems can transcribe speech to texts to save radiologists' time to type the report. However, transcription introduces an extra step to the process and thus associates with additional costs and errors.

Computer aided diagnosis (CAD) tools could significantly simplify the diagnosis procedure for radiologists and increase their work throughputs. For example, the CAD system can automatically detect suspicious regions in the images and classify/segment those regions for quantitative analysis to understand the implications. This procedure speeds up lesion detection and the overall diagnosis process, as well as increase accuracy. The CAD system can also present visualization of analysis results (e.g., bounding boxes, object boundary contours, surface rendering, volume rendering, etc.) to a user, e.g., the radiologist. These visualization results with quantitative analysis could become parts of a diagnosis report. Then radiologists/clinicians add their observations and diagnosis result to the reports. However, automatically generating reports from the CAD system is susceptible to misdiagnosis and lacks radiologists' inputs and decisions.

Embodiments of the disclosure address the above problems by designing an interactive diagnosis report system taking advantage of the auto-diagnosis of the CAD system as well as radiologists' inputs based on their experience.

SUMMARY

Embodiments of the disclosure provide a system for generating a diagnosis report based on a medical image of a patient. The system includes a communication interface configured to receive the medical image acquired by an image acquisition device. The system further includes at least one processor. The at least one processor is configured to detect a medical condition based on the medical image and automatically generate text information describing the medical condition. The at least one processor is further configured to construct the diagnosis report. The diagnosis report includes at least one image view showing the medical condition and a report view including the text information describing the medical condition. The system also includes a display configured to display the diagnosis report.

Embodiments of the disclosure also provide a method for generating a diagnosis report based on a medical image of a patient. The method includes receiving, by a communication interface, the medical image acquired by an image acquisition device. The method further includes detecting, by at least one processor, a medical condition based on the medical image and automatically generating, by the at least one processor, text information describing the medical condition. The method also includes constructing, by the at least one processor, the diagnosis report. The diagnosis report includes at least one image view showing the medical condition and a report view including the text information describing the medical condition. The method additionally includes displaying the diagnosis report on a display.

Embodiments of the disclosure further provide a non-transitory computer-readable medium having instructions stored thereon that, when executed by one or more processors, causes the one or more processors to perform a method for generating a diagnosis report based on a medical image of a patient. The method includes receiving the medical image acquired by an image acquisition device. The method further includes detecting a medical condition based on the medical image and automatically generating text information describing the medical condition. The method also includes constructing the diagnosis report. The diagnosis report includes at least one image view showing the medical condition and a report view including the text information describing the medical condition. The method additionally includes displaying the diagnosis report.

It is to be understood that both the foregoing general description and the following detailed description are exemplary and explanatory only and are not restrictive of the invention, as claimed.

DETAILED DESCRIPTION

Reference will now be made in detail to the exemplary embodiments, examples of which are illustrated in the accompanying drawings. Wherever possible, the same reference numbers will be used throughout the drawings to refer to the same or like parts.

Figure 1:
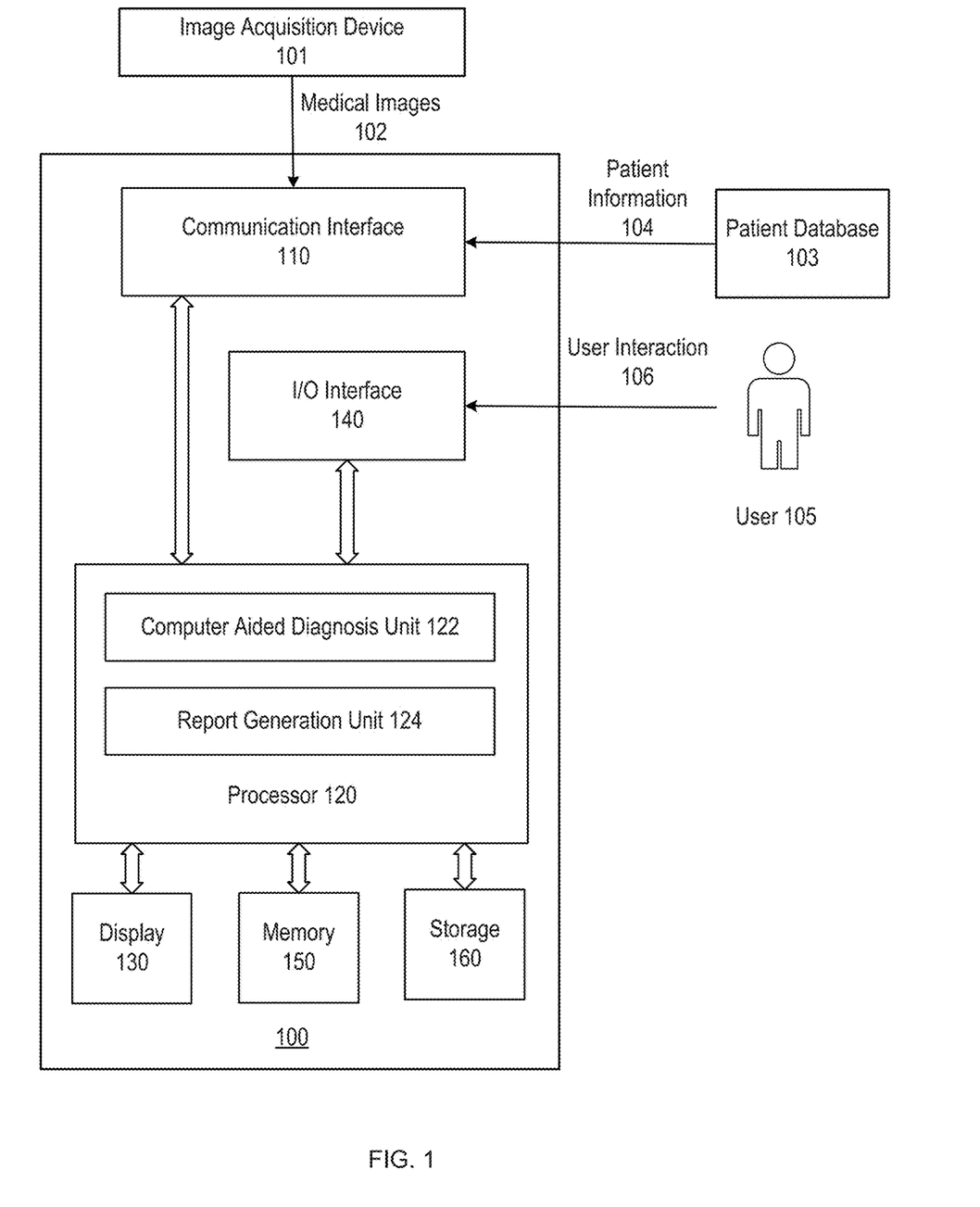
FIG. 1 illustrates a block diagram of an exemplary diagnosis report generating system, according to embodiments of the disclosure.

FIG. 1 illustrates a block diagram of an exemplary diagnosis report generating system 100, according to embodiments of the disclosure. Consistent with the present disclosure, diagnosis report generating system 100 is configured to generate a diagnosis report based on medical images 102 acquired by an image acquisition device 101. Consistent with the present disclosure, diagnosis report generating system 100 may receive medical images 102 from image acquisition device 101. Alternatively, medical images 102 may be stored in an image database first and diagnosis report generating system 100 may receive medical images 102 from the image database. In some embodiments, medical images 102 may be two-dimensional (2D) or three-dimensional (3D) images. A 3D image may contain multiple 2D image slices.

In some embodiments, image acquisition device 101 may acquire medical images 102 using any suitable imaging modalities, including, e.g., functional MRI (e.g., fMRI, DCE-MRI and diffusion MRI), Cone Beam CT (CBCT), Spiral CT, Positron Emission Tomography (PET), Single-Photon Emission Computed Tomography (SPECT), X-ray, optical tomography, fluorescence imaging, ultrasound imaging, and radiotherapy portal imaging, etc.

For example, image acquisition device 101 may be an MRI scanner. The MRI scanner includes a magnet that surrounds a patient tube with a magnetic field. A patient is positioned on a padded table that can move into the patient tube. The MRI scanner further includes gradient coils in multiple directions (e.g., x, y, and z directions) to create a spatially varying magnetic field on top of the uniform magnetic field created by the magnet. The uniform magnetic field used by the MRI scanner are typically between 0.2 T-7 T, e.g., around 1.5 T or 3 T. The MRI scanner also includes RF coils to excite the tissues inside the patient body and transceivers to receive electromagnetic signals generated by the tissues while returning to an equilibrium state.

As another example, image acquisition device 101 may be a CT scanner. The CT scanner includes an X-ray source that emits X-rays against body tissues and a receiver that receives the residual X-rays after attenuated by the body tissues. The CT scanner also includes rotating mechanism to capture X-ray images at different view angles. Such rotating mechanism can be a rotating table that rotates the patient, or a rotating structure that rotates the X-ray source and the receiver around the patient. The X-ray images at different angles are then processed by a computer system to construct a two-dimensional (2D) cross section image or a three-dimensional (3D) image.

Consistent with some embodiments, diagnosis report generating system 100 may further receive patient information 104 from patient database 103. Patient information 104 may be meta data recorded through patient registration or generated with medical image 102. For example, the meta data may include age and gender of the patient, patient medical history, and family medical history, etc. Patient database 103 may in include a volatile or non-volatile, magnetic, semiconductor, tape, optical, removable, non-removable, or other type of storage device or tangible (i.e., non-transitory) computer-readable medium including, but not limited to, a ROM, a flash memory, a dynamic RAM, and a static RAM. In some embodiments, patient database 103 may be located on-site with diagnosis report generating system 100 or off-site (i.e., remotely).

In some embodiments, as shown in FIG. 1, diagnosis report generating system 100 may include a communication interface 110, a processor 120, a display 130, an I/O interface 140, a memory 150, and a storage 160 and. In some embodiments, diagnosis report generating system 100 may have different modules in a single device, such as an integrated circuit (IC) chip (implemented as an application-specific integrated circuit (ASIC) or a field-programmable gate array (FPGA)), or separate devices with dedicated functions. In some embodiments, one or more components of diagnosis report generating system 100 may be located in a cloud, or may be alternatively in a single location (such as in a computer inside a radiologist's office) or distributed locations. Components of diagnosis report generating system 100 may be in an integrated device, or distributed at different locations but communicate with each other through a network (not shown).

Communication interface 110 may send data to and receive data from external systems or devices, such as image acquisition device 101 and patient database 103, via communication cables, a Wireless Local Area Network (WLAN), a Wide Area Network (WAN), wireless networks such as radio waves, a cellular network, and/or a local or short-range wireless network (e.g., Bluetooth™), or other communication methods. In some embodiments, communication interface 110 can be an integrated services digital network (ISDN) card, cable modem, satellite modem, or a modem to provide a data communication connection. As another example, communication interface 110 can be a local area network (LAN) card to provide a data communication connection to a compatible LAN. Wireless links can also be implemented by communication interface 110. In such an implementation, communication interface 310 can send and receive electrical, electromagnetic or optical signals that carry digital data streams representing various types of information via a network.

Consistent with some embodiments, communication interface 110 may receive medical images 102 acquired by image acquisition device 101. Consistent with some embodiments, communication interface 110 may also receive patient information 104 from patient database 103. Communication interface 110 may further provide the received medical images 102 and patient information 104 to storage 160 for storage or to processor 120 for processing.

Processor 120 may include any appropriate type of general-purpose or special-purpose microprocessor, digital signal processor, or microcontroller. Processor 120 may be configured as a stand-alone processor module dedicated to diagnosis report generation. Alternatively, processor 120 may be configured as a shared processor module for performing other functions unrelated to diagnosis report generation.

As shown in FIG. 1, processor 120 may include multiple modules, such as a computer aided diagnosis unit 122 (hereafter, "CAD unit 122"), and a report generation unit 124, and the like. These modules (and any corresponding sub-modules or sub-units) can be hardware units (e.g., portions of an integrated circuit) of processor 120 designed for use with other components or software units implemented by processor 120 through executing at least part of a program. The program may be stored on a computer-readable medium, and when executed by processor 120, it may perform one or more functions or operations. Although FIG. 1 shows units 122-124 both within one processor 120, it is contemplated that these units may be distributed among multiple processors located near or remotely with each other.

CAD unit 122 is configured to assist doctors in the interpretation of medical images. In some embodiments, CAD unit 122 may process digital images for typical appearances and to highlight conspicuous sections, such as possible diseases, in order to offer input to support a decision taken by the professional. For example, CAD unit 122 performs interactive/automated algorithms to detect conspicuous structures in a medical image 102 indicative of a medical condition.

In some embodiments, medical images 102 may be copied to CAD unit 122 in a DICOM-format. Pre-processing may be performed on medical images 102 such as filtering to reduce image artifacts or noises, and leveling image quality, e.g., by adjusting the image's different exposure parameters to increase contrast. CAD unit 122 may further segment the images to identify different regions of interest (e.g., anatomical structures) in the image, e.g. heart, lung, ribcage, blood vessels, possible round lesions. Various segmentation methods may be used, including, e.g., matching with an anatomic databank, or using neural networks trained using sample images. The identified structures may be analyzed individually for special characteristics.

In some embodiments, CAD unit 122 may perform a fully automatic; initial interpretation and triage of studies into some meaningful categories (e.g. negative and positive). Various classification algorithms may be used, including, e.g., the Nearest-Neighbor Rule (e.g. k-nearest neighbors), Minimum distance classifier, Cascade classifier, Naive Bayesian Classifier, Artificial Neural Network, Radial basis function network (RBF), Support Vector Machine (SVM) and Principle Component Analysis (PCA), etc. If the detected structures meet certain criteria, CAD unit 122 may highlight them in the image for the radiologist, for example, using boundary contours or bounding boxes. This allows the radiologist to draw conclusions about the condition of e pathology. In some embodiments, CAD unit 122 may further determine one or more parameters that quantify the medical condition. For example, the parameters may include size (such as diameter, length, width, depth, etc.), volume, pixel intensities, or the contrast characteristics of a tumor.

Accordingly, the output of CAD unit 122 may include object detection results (e.g. boundary contours or bounding boxes), segmentations, classification results etc. as well as quantitative analysis results (e.g. size, volume, gray-value distribution etc.) derived from those results. Report generation unit 124 is configured to perform report generation algorithms based on the output of CAD unit 122. In some embodiments, the diagnosis report may include various patient, examination, and diagnosis information. In some embodiments, the diagnosis report may be automatically or semi-automatically generated by report generation unit 124. In some embodiments, report generation unit 124 may generate the diagnosis report interactively with a user 105, e.g., a radiologist.

In some embodiments, report generation unit 124 may generate automated report content from meta data contained in patient information 104. For example, one part of the report may be composed of patient history information (such as name, gender, age of the patient) and scan information (such as imaging modality used to acquire medical image 102, the region scanned, and if any contrast agent is used) derived from the patient's meta data.

Report generation unit 124 may further generate diagnosis content of the report based on CAD system results. Report generation unit 124 infers text information of the report from CAD results, such as the object detection/segmentation/classification results. In some embodiments, the text information may indicate, among other things, the type of the detected object (i.e. bleeding type cerebral hemorrhage) and the position of the detected object (i.e. left frontal lobe). In some embodiments, the text information may further indicate results of quantitative analysis, such as diameters, volumes, and density distribution, etc.

In some embodiments, a text dictionary used to produce texts based on the detection results may be established. For example, the text dictionary may be trained using existing clinical reports. The training may be performed by processor 120 or a separate processor. In the training stage, the existing clinical reports may be mined to identify key words to describe image observations, including object properties, types, object locations, etc. According to some embodiments, based on the mined information, one or more lookup tables may be created for text query purpose. For example, Table 1 shows an example of object type lookup table, and Table 2 shows an example of object location lookup table.

TABLE 1

Example of object type lookup table

| ID | text |
|---|---|
| 0 | Cerebral Hemorrhage |
| 1 | Subarachnoid hemorrhage |
| 2 | Subdural hematoma |
| ... | ... |

TABLE 2

Example of object location lookup table

| Position Id | text |
|---|---|
| 0 | Left Frontal Lobe |
| 1 | Right Frontal Lobe |
| 2 | Left Back Lobe |
| ... | ... |

Based on the lookup tables and detection results provided by CAD unit 122, report generation unit 124 retrieves the text from the lookup tables and fills the corresponding sections in the report. It is contemplated that a lookup method is only one exemplary approach to automatically generate texts based on CAD detection results. Other methods can be used, such as a machine learning approach, e.g., sentence prediction from CAD results).

In some embodiments, the report may also include screenshots of 2D/3D visualization containing the detected objects. In some embodiments, the report may display and discuss the top N detected objects, where N is a predetermined number, e.g., 3, 5, 10, etc. If the number of detected objects is less than or equal to N, all detected objects are included the report. If the number of detected objects is more than N, all detected objects are included the report. For each detected object, the quantitative numbers may be computed and displayed in the report.

In some embodiments, report generation unit 124 may utilize the meta information to improve the diagnosis results provided by CAD unit 122. For example, CAD unit 122 may detect lung nodules and predict nodule malignancy based on medical image 102. Meta data such as age, smoking history, occupations, etc. may be used to improve the malignancy prediction of the nodule.

Processor 120 may render visualizations of user interfaces to display data on a display 130. Display 130 may include a Liquid Crystal Display (LCD), a Light Emitting Diode Display (LED), a plasma display, or any other type of display, and provide a Graphical User Interface (GUI) presented on the display for user input and data display. The display may include a number of different types of materials, such as plastic or glass, and may be touch-sensitive to receive commands from the user. For example, the display may include a touch-sensitive material that is substantially rigid, such as Gorilla Glass™, or substantially pliable, such as Willow Glass™.

Figure 2:
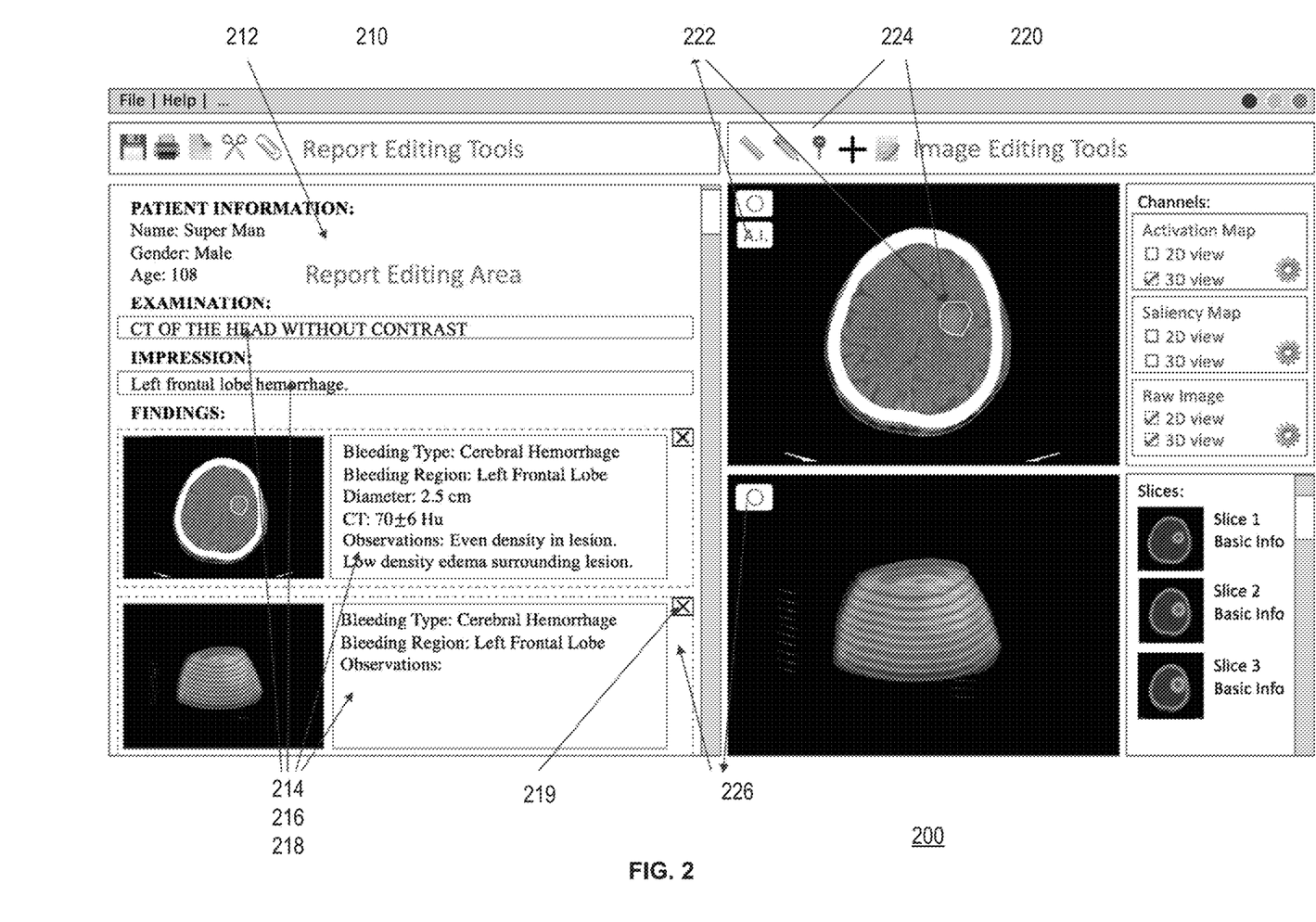
FIG. 2 illustrates an exemplary user interface of the diagnosis report generating system of FIG. 1, according to embodiments of the disclosure.
Figure 3:
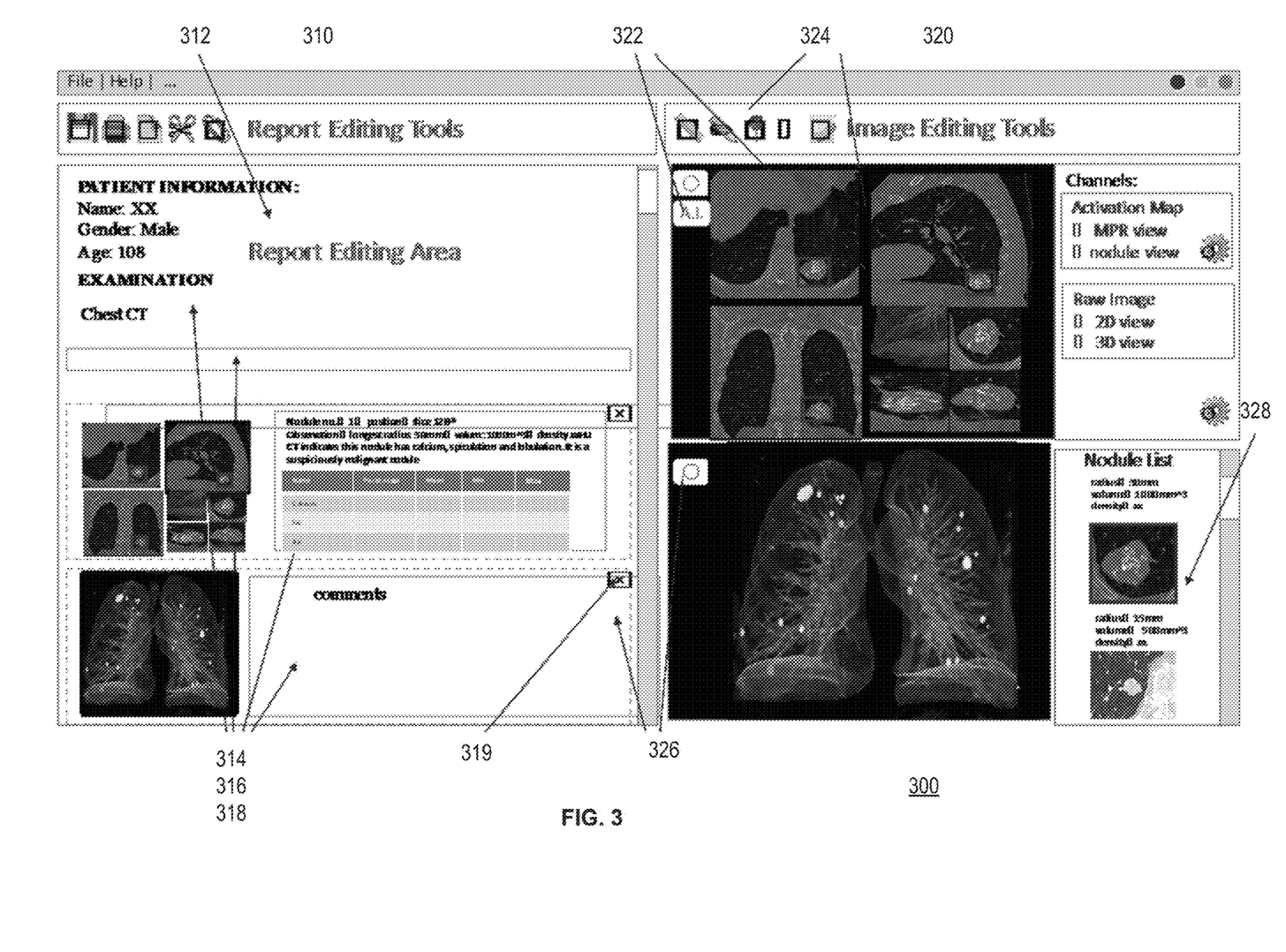
FIG. 3 illustrates another exemplary user interface of the diagnosis report generating system of FIG. 1, according to embodiments of the disclosure.

The visualization may include medical images and analysis results generated by CAD unit 122 as well as the diagnostic report generated by report generation unit 124. In some embodiments, the CAD results and the diagnostic report may be displayed side-by-side. For example, FIGS. 2-3 illustrate exemplary user interfaces 200/300 of diagnosis report generating system 100 of FIG. 1, according to embodiments of the disclosure. User interfaces 200/300 may include a report view 210/310 displaying the diagnosis report generated by report generation unit 124, and a CAD view 220/320 displaying images and detection results produced by CAD unit 122. It is contemplated that the relative positions and configurations of the views are exemplary only, and may be re-arranged in other embodiments.

As shown in FIGS. 2-3, CAD view 220/320 shows medical images rendered in views to show the detected object. For example, CAD view 220 in FIG. 2 shows a 3D brain image containing multiple image slices in the bottom, and a selected image slice on the top. A cerebral lesion is highlighted using a different color as well as marked by a boundary contour. As another example, CAD view 320 in FIG. 3 shows a 3D lung image in the bottom, and 3 cross-sectional views (i.e., sagittal, coronal, transverse views) of image at a selected point. The exemplary image shown in CAD view 320 includes multiple lung nodules. The lung nodules are highlighted, e.g., each by a bounding box, in the respective 3 cross-sectional views in CAD view 320. In some embodiments, the 3D viewer in CAD view 220 presents volume rendering, surface rendering and multi-planar reconstructions (MPR) and curved MPR (for vessel visualization).

Report view 210/310 includes a patient information section 212/312 displaying patient information derived from meta data, such as name, gender, and age of the patient. According to some embodiments, report view 210/310 further includes an examination section 214/314 describing the scan information such as the image modality used to acquire medical image 102, the part of the patient body scanned, and any contrast agent used in the scan. In some embodiments, report view 210/310 also includes an impression section 216/316 displaying the diagnosis results, e.g., indicating a medical condition of the patient, based on the CAD analysis. Report view 210/310 may further include a findings section 218. In some embodiments, findings section 218/318 may display screenshots of medical images with the detected object highlighted, e.g., by a boundary contour or a bounding box, as shown in CAD view 220/320. In some embodiments, findings section 218/318 may further include texts describing the type of detected object (e.g., cerebral hemorrhage, lung nodules) and its location (e.g., left frontal lobe, etc.).

In some embodiments, findings section 218/318 may also show the parameters that quantify the medical condition, such as the size, volume, and intensity distribution of the detected object, as well as other observations. For example, as shown in findings section 218, the diameter of the detected lesion in the left frontal lobe is measured as 2.5 cm. Additional observations include, e.g., that the lesion has an even density, and that the edema surrounding lesion has a low density. For example, as shown in findings section 318, the longest radius of the detected lung nodule may be 30 mm, and its volume might be 1000 m$^3$. Additional observations include that the nodule has calcium, spiculation and lobulation, and thus is a suspiciously malignant nodule.

In some embodiments, automatically produced report may not always be sufficient for the clinical usage as it lacks a radiologist's/clinician's decision. In some embodiments, diagnosis report generating system 100 may provide interactive tools in the user interfaces displayed by display 130, to allow the radiologist/clinician to edit the CAD results and/or the diagnosis report. Returning to FIG. 1, in some embodiments, user 105 may provide a user interaction 106 via I/O interface 140. I/O interface 140 may be an input/output device that is configured to receive user input or provide system output to the user. For example, I/O interface 140 may be a keyboard, a mouse, a click button, a stylus, a touch-screen, a microphone, or any combination thereof.

In some embodiments, user interaction 106 may be performed in CAD view 220/320 to edit the CAD results. For example, user interaction 106 may be user 105 selecting an image slice from a 3D image (e.g., shown in CAD view 220) or selecting a detected object from an object list (e.g., selecting a lung nodule from a nodule list 328 shown in CAD view 320). As another example, user interaction 106 may further include user 105 manually drawing a ruler/curve/region/point/bounding box/text in the view by using image editing tools 224/324.

If user 105 is satisfied with the editing, he could drag the view(s) shown in CAD view 220/320 into the report, or click a "send" button 226/326 to send the images shown in CAD view 220/320 view to report view 210/310, to be included in, e.g., findings section 218/318. In some embodiments, both 2D and 3D image editing are supported. In addition, user 105 may click on an "A. I." button 222/322 to cause CAD unit 122 to perform the quantitative analysis again based on the user edits to the images, and send the updated parameters to report view 210/310 to update, e.g., findings section 218/318. In some embodiments, the user interactions with CAD view 220/320 may automatically update the content of the report based on user interaction 106, without user 105 having to drag or click on any button.

In some embodiments, user interaction 106 may also include interactions with report view 210/310. For example, each of sections 212-218 and 312-318 may be editable by user 105. An editable area in the diagnosis report allows user 105 (e.g., a radiologist/clinician) to add, modify, or delete the report content. In some embodiments, user 105 could remove the automatically generated texts and screenshots, such as by clicking on a cancel button 219/319. In addition, user 105 can edit any text section in the diagnosis report to provide his independent diagnosis based on medical images 102. In one embodiment, the text input is through a keyboard (one embodiment of I/O interface 140). In another embodiment, the text input is through a microphone (one embodiments of I/O interface 140) and processor 120 may perform a speech to text translation to transcribe the audio input into texts.

In some embodiments, user interfaces 200/300 may provide additional functionalities such as preview, print, email or archive. For example, user 105 may double-click on the diagnosis report to finalize it, save it to memory 150/storage 160, and send it to another department via email.

Memory 150 and storage 160 may include any appropriate type of mass storage provided to store any type of information that processor 120 may need to operate. Memory 150 and/or storage 160 may be a volatile or non-volatile, magnetic, semiconductor, tape, optical, removable, non-removable, or other type of storage device or tangible (i.e., non-transitory) computer-readable medium including, but not limited to, a ROM, a flash memory, a dynamic RAM, and a static RAM. Memory 150 and/or storage 160 may be configured to store one or more computer programs that may be executed by processor 120 to perform functions disclosed herein. For example, memory 150 and/or storage 160 may be configured to store program(s) that may be executed by processor 120 for CAD analysis and diagnosis report generation.

Memory 150 and/or storage 160 may be further configured to store information and data used by processor 120. For instance, memory 150 and/or storage 160 may be configured to store medical images 102 acquired by image acquisition system 101, and patient information 104 provided by patient database 103. Memory 150 and/or storage 160 may also store CAD analysis results generated by CAD unit 122, as well intermediary data created during the CAD process. Memory 150 and/or storage 160 may also store various parts of a diagnosis report generated by report generation unit 124, such as images, tables, and texts, etc. The various types of data may be stored permanently, removed periodically, or disregarded immediately after each frame of data is processed.

Figure 4:
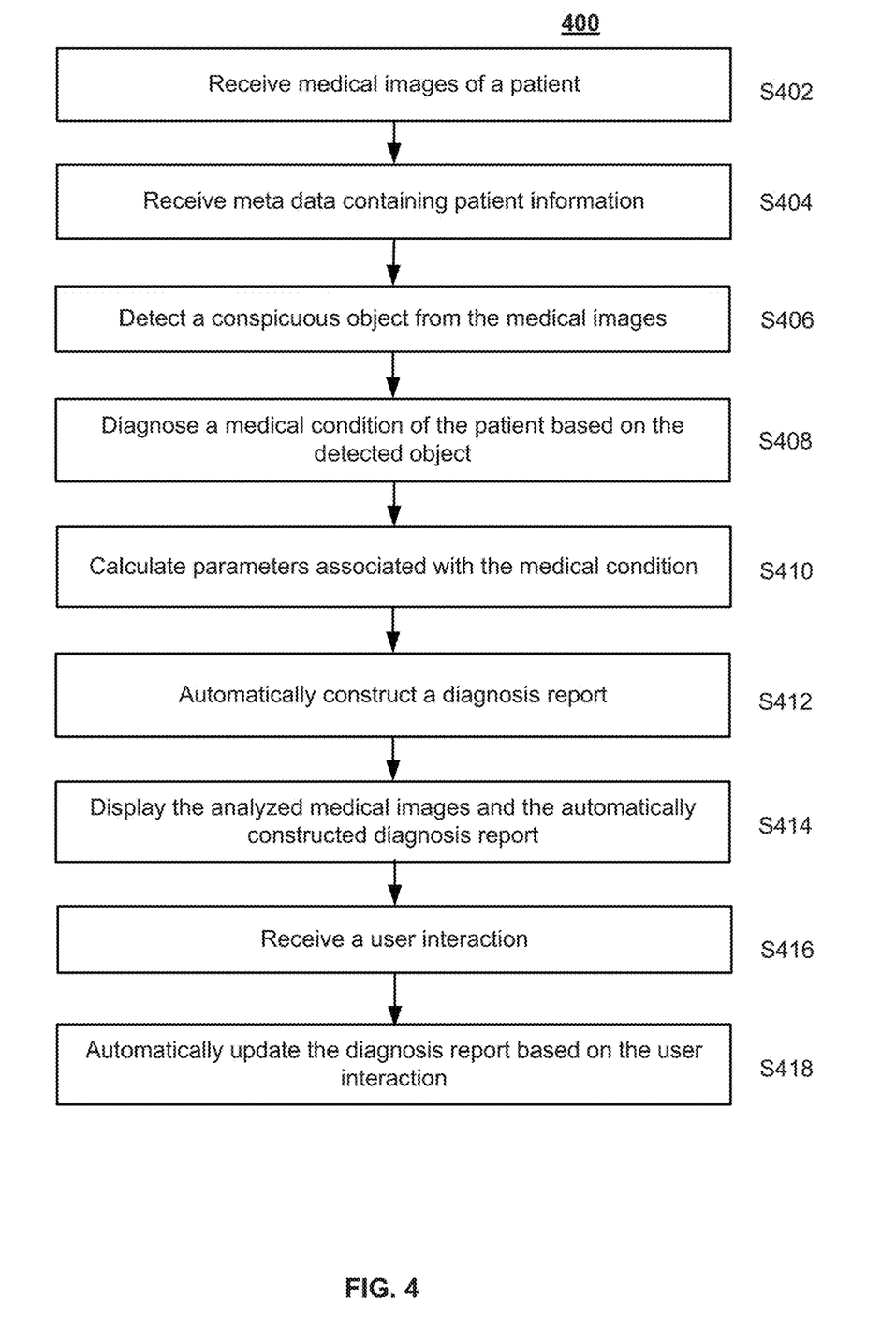
FIG. 4 shows a flow chart of an exemplary method for generating a diagnosis report, according to embodiments of the disclosure.

FIG. 4 shows a flow chart of an exemplary method 400 for generating a diagnosis report, according to embodiments of the disclosure. For example, method 400 may be implemented by diagnosis report generating system 100 in FIG. 1. However, method 400 is not limited to that exemplary embodiment. Method 400 may include steps S402-S418 as described below. It is to be appreciated that some of the steps may be optional to perform the disclosure provided herein. Further, some of the steps may be performed simultaneously, or in a different order than shown in FIG. 4.

In step S402, diagnostic report generating system 100 receives one or more medical images 102 associated with a patient, e.g., from image acquisition device 101 or a medical image database. Medical images 102 may be 2D or 3D images. Medical images 102 can be of any imaging modality among functional MRI (e.g., fMRI, DCE-MRI and diffusion MRI), Cone Beam CT (CBCT), Spiral CT, Positron Emission Tomography (PET), Single-Photon Emission Computed Tomography (SPECT), X-ray, optical tomography, fluorescence imaging, ultrasound imaging, and radiotherapy portal imaging, etc., or the combination thereof. In some embodiments, medical image 102 may be taken with contrast agent to enhance the image contrast. In step S404, diagnostic report generating system 100 receives patient information 104 from patient database 103. For example, patient information 104 may include age and gender of the patient, patient medical history, and family medical history, etc. Although S404 is illustrated as following S402 in FIG. 4, it is contemplated that S402 and S404 can be performed in any order relative to each other, or simultaneously with each other.

In step S406, diagnostic report generating system 100 detects a suspicious object from medical images 102. In some embodiments, CAD unit 122 may be used to perform a CAD analysis to detect the conspicuous object. The conspicuous object may be a lesion, a tumor, or another anatomical structure that is potentially indicative of a medical condition of the patient that needs to be treated. For example, the conspicuous object may be a cerebral lesion as shown in FIG. 2 or one or more lung nodules as shown in FIG. 3. To detect the conscious object, CAD unit 122 may perform pre-processing, image segmentation, and classification, etc., as described in detail above in connection with FIG. 1. In some embodiments, the detected object may be highlighted in medical image 102 for the radiologist, for example, using boundary contours or bounding boxes.

In step S408, diagnostic report generating system 100 diagnoses a medical condition of the patient based on the detected object. The medical condition may be, e.g., that the detected object region is bleeding, or that the detected object is a tumor indicative of a cancer. In some embodiments, diagnostic report generating system 100 may diagnose the medical condition automatically, e.g., using classification methods. For example, the detected object may be classified between negative (e.g., tumor) or positive (e.g., benign). Various classification algorithms may be used including the Nearest-Neighbor Rule (e.g. k-nearest neighbors), Minimum distance classifier, Cascade classifier, Naive Bayesian Classifier, Artificial Neural Network, Radial basis function network (RBF), Support Vector Machine (SVM)' and Principle Component Analysis (PCA), etc. In some embodiments, automatic diagnosis may be performed using machine learning methods, such as based on a neural network trained using sample images and known conditions. Applying the neural network to the detected object, CAD unit 122 may determine a medical condition and the probability of the medical condition exists within the patient. For example, CAD unit 122 may determine the patient has a 90% probability of having lung cancer. In some embodiments, the diagnosis may be made semi-automatically, e.g., combined with inputs from radiologists.

In step S410, diagnostic report generating system 100 calculates quantitative parameters associated with the medical condition. The parameters quantify and describe the medical condition. In some embodiments, the parameters nay include size (such as diameter, length, width, depth, etc.), volume, pixel intensities, or the contrast characteristics of a tumor. For example, the diameter of a cerebral lesion in FIG. 3 is 2.5 cm, which indicates severity of the hemorrhage condition in the left frontal lobe. In some embodiments, the parameters may be determined partially based on a user input, e.g., from a radiologist. For example, the radiologist may manually measure the parameters using a ruler provided by user interface 200/300.

In step S412, diagnostic report generating system 100 automatically constructs a diagnosis report. In some embodiments, construction of the diagnosis report may be performed by report generation unit 124. In some embodiments, report generation unit 124 may generate automated report content using patient information 104. For example, the report may include a patient information section 212/312 showing patient name, gender, and age, as well as examination section 214 containing scan information derived from the patient's meta data. Report generation unit 124 may further generate diagnosis content of the report based on step S408. For example, the diagnosis report may include impression section 216/316 and findings section 218/318. The diagnosis sections in the report may include screenshots of images imported from the CAD analysis as well as text information indicating, e.g., the type of the detected object (i.e. bleeding type cerebral hemorrhage), the position of the detected object (i.e. left frontal lobe), and parameters calculated in step S410. In some embodiments, the text information may be determined based on lookup tables such as shown in Tables 1 and 2. In some embodiments, report generation unit 124 may utilize the meta information to improve the diagnosis results provided by CAD unit 122. For example, CAD unit 122 may detect lung nodules and predict nodule malignancy solely based on medical image 102. As part of step S412, report generation unit 124 may use meta data such as age, smoking history, occupations, etc. to improve the malignancy prediction of the nodule.

In step S414, diagnostic report generating system 100 displays the analyzed medical images and the automatically constructed diagnosis report, e.g., on display 130. In some embodiments, the medical images and the diagnosis report may be displayed side-by-side. In some embodiments, the medical images are displayed with the detected objects highlighted, e.g., using boundary contours or bounding boxes or enhanced colors. In some embodiments, when more than N conspicuous objects are detected, the top N objects may be displayed.

In step S416, diagnostic report generating system 100 receives user interaction 106. In some embodiments, user 105 may provide a user interaction 106 via I/O interface 140. In some embodiments, user 105 may edit the CAD results. For example, user interaction 106 may be user 105 selecting an image slice from a 3D image or selecting a detected object from an object list (e.g., selecting a lung nodule from a nodule list). As another example, user interaction 106 may further include user 105 manually drawing a ruler/curve/region/point/bounding box/text in the view by using image editing tools. As yet another example, user interaction 106 may also include sending or dragging the images shown in a CAD view and/or parameters calculated based on the CAD analysis to be included in the diagnosis report. In some embodiments, user interaction 106 may also include interactions with the report itself. For example, the diagnosis report may include one or more editable areas. An editable area in the diagnosis report allows user 105 (e.g., a radiologist/clinician) to add, modify, or delete the report content.

In step S418, diagnostic report generating system 100 automatically updates the diagnosis report based on the user action. In some embodiments, when user 105 selects a different image slice (e.g., from a 3D image) or a different detected object (e.g., another lung nodule in the image), report generation unit 124 accordingly updates the screenshots included in the diagnosis report. In some embodiments, report generation unit 124 automatically recalculates the quantitative parameters based on the edits made to the images. User edits to the report itself may be incorporated or otherwise reconciled with the existing report.

Another aspect of the disclosure is directed to a non-transitory computer-readable medium storing instructions which, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

It will be apparent to those skilled in the art that various modifications and variations can be made to the disclosed system and related methods. Other embodiments will be apparent to those skilled in the art from consideration of the specification and practice of the disclosed system and related methods.

It is intended that the specification and examples be considered as exemplary only, with a true scope being indicated by the following claims and their equivalents.

What is claimed is:

1. A system for generating a diagnosis report based on a medical image of a patient, comprising:

a communication interface configured to receive the medical image acquired by an image acquisition device using an imaging modality selected from the group consisting of computed tomography (CT), magnetic resonance imaging (MRI), functional MRI, cone beam computed tomography (CBCT), spiral CT, positron emission tomography (PET), single-photon emission computed tomography (SPECT), X-ray, optical tomography, fluorescence imaging, ultrasound imaging, or radiotherapy portal imaging;

at least one processor configured to:
  detect a medical condition of the patient based on the medical image;
  automatically generate text information describing the medical condition; and
  construct the diagnosis report, wherein the diagnosis report includes at least one image view showing the medical condition and a report view including the text information describing the medical condition; and a display configured to display the diagnosis report.

2. The system of claim 1, wherein to detect the medical condition, the at least one processor is further configured to:
  detect a conspicuous object from the medical image; and
  diagnose the medical condition of the patient based on the conspicuous object.

3. The system of claim 2, wherein the at least one processor is further configured to highlight the conspicuous object in the at least one image view of the diagnosis report.

4. The system of claim 1, wherein the at least one processor is further configured to determine a probability that the medical condition exists within the patient,
  wherein the diagnosis report further includes the probability.

5. The system of claim 1, wherein to automatically generate the text information describing the medical condition, the at least one processor is configured to use a text dictionary storing key words describing image observations.

6. The system of claim 5, wherein the text dictionary is saved in a lookup table, wherein the at least one processor is configured to query the lookup table for corresponding key words based on the medical condition detected from the medical image and generate the text information using the key words.

7. The system of claim 1, wherein the report view further includes scan information describing the imaging modality used to acquire the medical image.

8. The system of claim 1, wherein the at least one processor is further configured to determine one or more quantitative parameters of the medical condition,
  wherein the text information includes the one or more quantitative parameters of the medical condition.

9. The system of claim 1, wherein the communication interface is further configured to receive meta data along with the medical image of the patient,
  wherein at least one processor is configured to automatically generate patient information based on the meta data,
  wherein the report view further includes the patient information.

10. The system of claim 1, wherein the diagnosis report displays the at least one image view and the generated text information side-by-side.

11. A method for generating a diagnosis report based on a medical image of a patient, comprising:
  receiving, by a communication interface, the medical image acquired by an image acquisition device using an imaging modality selected from the group consisting of computed tomography (CT), magnetic resonance imaging (MRI), functional MRI, cone beam computed tomography (CBCT), spiral CT, positron emission tomography (PET), single-photon emission computed tomography (SPECT), X-ray, optical tomography, fluorescence imaging, ultrasound imaging, or radiotherapy portal imaging;

detecting, by at least one processor, a medical condition based on the medical image;

automatically generating, by the at least one processor, text information describing the medical condition; and constructing, by the at least one processor, the diagnosis report, wherein the diagnosis report includes at least one image view showing the medical condition and a report view including the text information describing the medical condition; and displaying the diagnosis report on a display.

12. The method of claim 11, wherein detecting the medical condition further comprises:

detecting a conspicuous object from the medical image; and diagnosing the medical condition of the patient based on the conspicuous object.

13. The method of claim 12, further comprising highlight the conspicuous object in the at least one image view of the diagnosis report.

14. The method of claim 11, wherein detecting the medical condition further comprises determining a probability that the medical condition exists within the patient, wherein the diagnosis report further includes the probability.

15. The method of claim 11, wherein automatically generating the text information describing the medical condition further comprises:

querying a text dictionary for corresponding key words based on the medical condition detected from the medical image; and generating the text information using the key words.

16. The method of claim 11, wherein the report view further includes scan information describing the imaging modality used to acquire the medical image.

17. The method of claim 11, further comprising determining one or more quantitative parameters of the medical condition, wherein the text information includes the one or more quantitative parameters of the medical condition.

18. The method of claim 11, further comprising:

receiving meta data along with the medical image of the patient; and automatically generating patient information based on the meta data, wherein the report view further includes the patient information.

19. A non-transitory computer-readable medium having a computer program stored thereon, wherein the computer program, when executed by at least one processor, performs a method for generating a diagnosis report based on a medical image of a patient, comprising:

receiving the medical image acquired by an image acquisition device using an imaging modality selected from the group consisting of computed tomography (CT), magnetic resonance imaging (MRI), functional MRI, cone beam computed tomography (CBCT), spiral CT, positron emission tomography (PET), single-photon emission computed tomography (SPECT), X-ray, optical tomography, fluorescence imaging, ultrasound imaging, or radiotherapy portal imaging;

detecting a medical condition based on the medical image;

automatically generating text information describing the medical condition; and constructing the diagnosis report, wherein the diagnosis report includes at least one image view showing the medical condition and a report view including the text information describing the medical condition; and displaying the diagnosis report.

20. The non-transitory computer-readable medium of claim 19, wherein automatically generating the text information describing the medical condition further comprises:

querying a text dictionary for corresponding key words based on the medical condition detected from the medical image; and generating the text information using the key words.

* * * * *